US005422271A

United States Patent [19]

Chen et al.

[11] Patent Number: 5,422,271

[45] Date of Patent: Jun. 6, 1995

[54] NUCLEIC ACID MATERIAL AMPLIFICATION AND DETECTION WITHOUT WASHING

[75] Inventors: Paul H.-D. Chen, Boston, Mass.; John B. Findlay, Rochester, N.Y.; Susan M. Atwood, Newark, N.Y.; Lynn Bergmeyer, Rochester, N.Y.

[73] Assignee: Eastman Kodak Company, Rochester, N.Y.

[21] Appl. No.: 979,569

[22] Filed: Nov. 20, 1992

[51] Int. Cl.[6] .................... C12M 1/00

[52] U.S. Cl. .................... 435/287; 206/223; 206/569; 422/57; 422/58; 435/6; 435/91.2; 435/291

[58] Field of Search .................... 435/287, 288; 206/223, 206/568, 569; 422/57, 58

[56] References Cited

U.S. PATENT DOCUMENTS 5,147,609 9/1992 Grenner .................... 422/58

FOREIGN PATENT DOCUMENTS 381501 8/1990 European Pat. Off. .

OTHER PUBLICATIONS

Whessell et al, Comparison of Three Nonradioisotopic Polymerase Chain Reaction-Based Methods for Detection of Human Immunodeficiency Virus Type I. *J. Clin. Microbiology*, vol. 30, pp. 845–853 (Apr. 1992).

*Primary Examiner*—Margaret Parr
*Assistant Examiner*—Scott W. Houtteman
*Attorney, Agent, or Firm*—Dana M. Schmidt

[57] ABSTRACT

A device and method are disclosed for amplifying and detecting nucleic acid material. The device and method use a label and signalling material responsive to the label to produce a detectable signal. A surprising result of the method and device is that at least one of the wash steps heretofore required has been eliminated without substantially adversely affecting the results.

3 Claims, 8 Drawing Sheets

NUCLEIC ACID MATERIAL AMPLIFICATION AND DETECTION WITHOUT WASHING

FIELD OF THE INVENTION

This invention relates to reaction pouches or devices and methods used to amplify and detect nucleic acid materials.

BACKGROUND OF THE INVENTION

DNA detection is described in European Patent Application 381,501 using a method wherein PCR amplification of miniscule amounts of nucleic acid material, and detection of the amplified material can all occur in a single pouch that keeps the amplified material from escaping. Six temporarily-sealed blisters, also called compartments, are provided along with passageways connecting them to a detection site in a detection compartment. The blisters provide, in order, a PCR reaction compartment; a first wash compartment; an enzyme-labeling compartment containing, e.g., streptavidin horseradish peroxidase (hereinafter SA-HRP); a second wash compartment; a compartment containing signalling material responsive to the enzyme; and a stop solution compartment. Each of these is caused to empty into the detection compartment in the order indicated, where a detection site is used to capture the amplified nucleic acid material and to generate a detectable signal.

The use of the two wash compartments to provide two wash steps is consistent with all conventional approaches to detecting nucleic acid material. For example, Vol. 30 of *J. Clin. Microbiol,* 845–853 (April, 1992) describes a process used by Roche (p. 846–847) as being one in which, following hybridization of biotinylated product to the solid wall surface, "we washed the plate 4 times with wash Buffer I to remove any unhybridized product". These four washes correspond to the first wash step of the first wash blister of the pouch of European Patent Application 381,501, since there also, any DNA or nucleic acid material "unhybridized" to the detection sites is washed off. Thereafter, the Roche procedure incubates "at 37° C. for 15 minutes with an avidin-horseradish peroxidase conjugate", which of course corresponds to the emptying of the enzyme blister of the EPA pouch for the very same purpose. Thereafter, the Roche procedure" again washed the plate four times" "to remove unbound conjugate." This, of course, corresponds to the second wash step provided by the second wash blister disposed between the enzyme blister and the signalling material blister in the pouch of EPA 381,501.

Such procedures, with all the washes, although quite workable, are time consuming and therefore expensive. Further, the washes introduce complications into the manufacture of the pouch. However, they have been considered essential in order to eliminate "nonspecific signal," that is, signal that occurs because of either the presence of unbound nucleic acid material that is NOT the target, and/or unbound SA-HRP that should not be present because the target nucleic acid material is not present.

Thus, there has been a need prior to this invention to come up with a detection sequence that eliminates at least one, and preferably both, of the wash steps and wash blisters heretofore needed, without causing so much noise in the detection as to make the signal unreliable.

RELATED APPLICATIONS

Commonly-owned U.S. patent application Ser. No. 810,945, filed on Dec. 19, 1991 by J. Chemelli and entitled "Methods for Preventing Air Injection Into a Detection Chamber Supplied With Injection Liquid" discloses, but does not claim, the elimination of one of the two wash steps in the use of a pouch that provides PCR amplification and detection. That information was derived from the instant invention.

SUMMARY OF THE INVENTION

We have discovered that the format of the pouch used in the methods described in EPA 381,501 lends itself to eliminating one or both of the wash blisters, while providing substantially the same result. This was particularly surprising, given the substantial history that has dictated that washes are an essential step.

More specifically, in accord with one aspect of the invention, there is provided a method of detecting amplified nucleic acid material by hybridizing such material to a detection site comprising at least one immobilized probe, labeling the hybridized and now-immobilized nucleic acid material by bringing to the site a label that is or interacts with a signalling material to produce a signal, and thereafter adding the signalling material to the site to produce a detectable signal. The method is improved in that either the labeling step is used directly after the hybridizing step without requiring a wash step in between, or the adding step is used directly after the labeling step without requiring a wash step in between. As will be apparent, "either-or" used in this context is the non-exclusive use.

In accord with another aspect of the invention, there is provided a device for amplifying and detecting nucleic acid material by using at least one target strand as a template, the device comprising a reaction compartment for amplifying a sample of nucleic acid material, a detection site for detecting amplified nucleic acid material, and storage compartments containing signalling material and a label effective to generate, in combination, a detectable signal, and passageways for fluidly connecting the compartments with the site: The device is improved in that the device further includes no more than one wash compartment containing a wash liquid substantially free of reagents used in the storage or reaction compartments, and no more than one passageway connecting the wash compartment to the detection site, so that no more than one wash step is used in a sequence of steps comprising the emptying and moving of the contents of the compartments to the detection site.

Accordingly, it is an advantageous, unexpected feature of the invention that a method and device for amplifying and detecting nucleic acid material are provided which avoid at least one of the washes heretofore considered necessary to produce the desired result.

Other advantageous features will become apparent upon reference to the following Detailed Description, when read in light of the attached drawings.

DETAILED DESCRIPTION OF THE PREFERRED EMBODIMENTS

The description hereinafter sets forth the invention in the context of its preferred embodiments, in which a flexible pouch or device is provided and used in the manner taught in commonly-owned, now allowed U.S. patent application Ser. No. 673,053, filed on Mar. 21, 1991 by P. Schnipelsky et al, the details of which are expressly incorporated herein. (Some of that disclosure is the same as that which appears in EPA 381,501.) In addition, the invention is useful regardless of whether PCR amplification is used or not, and regardless of the presence of all the features of that pouch, provided that no more than one wash compartment is included with no more than one intervening wash step as a result.

As used herein, "wash" or "wash solution" means, a solution substantially free of capture, label and signal-forming reagents used in the other compartments, i.e., in either the label compartment or the signalling material compartment.

The ability of the flexible pouch of the aforesaid U.S. patent application Ser. No. 673,053 to provide the elimination of the wash step without seriously resulting in nonspecific signal, is not completely understood. It is thought, however, that it results from the construction of the pouch in a way that causes a linear passage of a slug of each successive liquid such that the front of the "slug" acts to wash off unbound reagents left by the previous "slug". Any interaction that occurs at such "front" is of little or no consequence to the signal developed at the immobilized sites. Furthermore, all of each slug of liquid passes over the detection site(s), improving the efficiency. The optional shear-thinning gel that can be added as described hereinafter enhances this capability, in that it appears to create a more viscous slug that retards backward migration of the components that are removed by the slug's front boundary.

Figure 1:
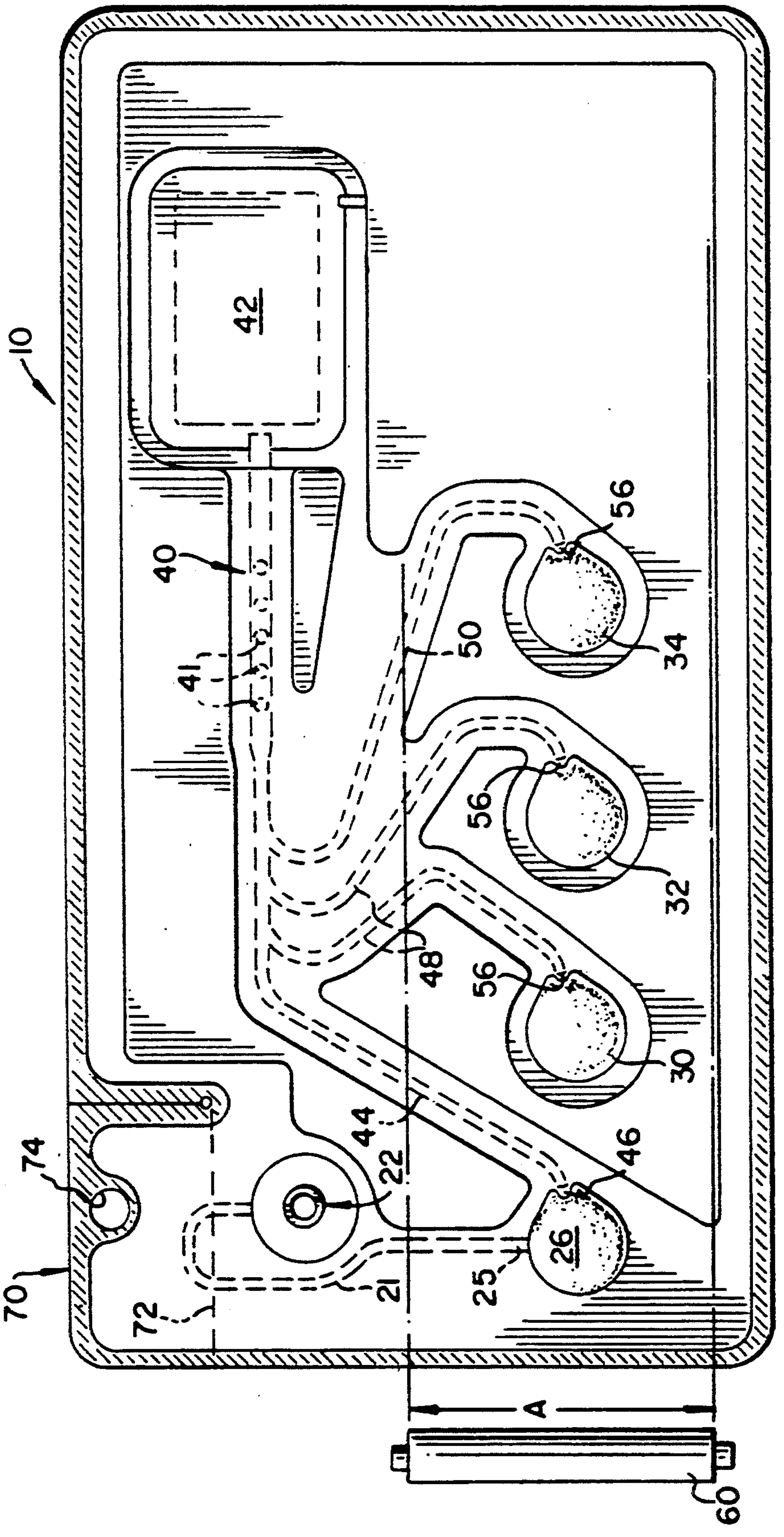
FIG. 1 is a plan view of a reaction device constructed in accordance with the invention.

FIG. 1 illustrates one form of this invention, in which the wash compartment and wash step in between the reaction compartment and the label compartment has been eliminated. A reaction cuvette or device 10 comprises an inlet port 22 for injection of patient sample liquid, which connects via a passageway 21 to a PCR reaction compartment 26. A seal 46 temporarily blocks flow out of compartment 26. When seal 46 is broken, liquid feeds via a passageway 44 to a detection chamber 40 having sites 41 comprising, preferably, beads anchored in place which will complex with any targeted analyte passing them from compartment 26, and then with reagents coming from the other reagent compartments. Those other compartments are compartments 30, 32, 34, each feeding via passageways 48 and 50 to chamber 40. Each of those passageways is temporarily sealed at 56, and contains an appropriate reagent liquid.

The details of the chemicals useful in all the compartments, and at the sites 41, are explained in more detail in the aforesaid U.S. patent application Ser. No. 673,053. The wash compartment preferably comprises a buffer, surfactants, EDTA, NaCl, and other salts.

In accordance with this invention, the number of necessary compartments has been simplified. Hence:

Compartment 26, in addition to the patient sample added by the user, preferably includes all the conventional reagents needed for PCR amplification, optionally kept in place by temporary seal 25. (The reagents can be pre-incorporated, or added with the patient sample as the latter is introduced.) The reagents include primers that are bound to one member of a binding pair, the other member of which appears in compartment 30 described below. A useful example of the binding member attached to a primer is biotin. (If present, Seal 25 is burst by injecting sample.)

Compartment 30 comprises, preferably, a label such as an enzyme bound to a complexing agent, such as avidin, that is a member of a binding pair, the other member of that pair being bound to a primer that becomes part of a targeted analyte during amplification in the reaction compartment 26 as described above. Hence, a useful reagent in compartment 30 is streptavidin horseradish peroxidase (hereinafter, SA-HRP). The other member of that binding pair is then biotin.

Labels other than enzymes are also useful. For example, fluorescent, radioactive, and chemiluminescent labels are also well-known for such uses. Chemiluminescent labels also preferably use a compartment 34 containing signalling reagent, discussed below for enzyme labels.

Compartment 32 preferably comprises a wash solution as the reagent.

Compartment 34 preferably comprises signalling material, and any dye stabilizing agent that may be useful. Thus, for example, a useful reagent solution in compartment 34 is a solution of a leuco dye that is a conventional substrate for the enzyme of compartment 30. $H_2O_2$ and any shear-thinning gels are also included.

Compartment 42 is a waste-collecting compartment, optionally containing an absorbant.

Roller 60 exemplifies the exterior pressure means used to burst each of the compartments sequentially, to sequentially advance the contents of the respective compartment to detection chamber 40. Because all of the compartments and passageways remain sealed during the processing, no leakage out of the device occurs and carry-over contamination is prevented. Sealing of port 22 is achieved by folding corner 70 about fold line 72, so that hole 74 fits over port 22 and passageway 21 is pinched off. A closure cap is then used to keep corner 70 so folded.

A useful processor to process device 10 is shown in EPA 402,994. Such a processor uses a support surface on which devices 10 are placed in an array, and pressure members, e.g., rollers, are mounted in position to process each of the cuvettes in parallel. The rollers are journalled several to one or more axles for convenience, these axles being incrementally advanced by gearing. Preferably, the support surface is horizontal or tilted up to about 15° from horizontal. Additionally, heaters can be optionally included, either in stationary form or carried with the rollers.

Thus, one and only one wash compartment 32 is used, to provide a wash step after incubation of the SA-HRP at the sites 41 of compartment 40, to remove any unbound SA-HRP. It is thought that no wash step or wash liquid needs to be provided between the respective sequential movements of the amplified nucleic acid material and the SA-HRP, to sites 41, for the reason that each reagent directed to the detection site is effectively washed out by the next reagent entering the station. It is surprising that the small volume in each compartment is adequate to do this.

Alternatively (not shown), the exact same structure of FIG. 1 is useful but with the wash liquid being located only in compartment 30, so that the SA-HRP is now located in compartment 32. In this configuration, the method proceeds to directly interact the signalling material of compartment 34 with sites 41 immediately after incubation of the SA-HRP at those sites, with no intervening wash. The reasons why this can be done are those set forth for the previous embodiment.

Figure 2:
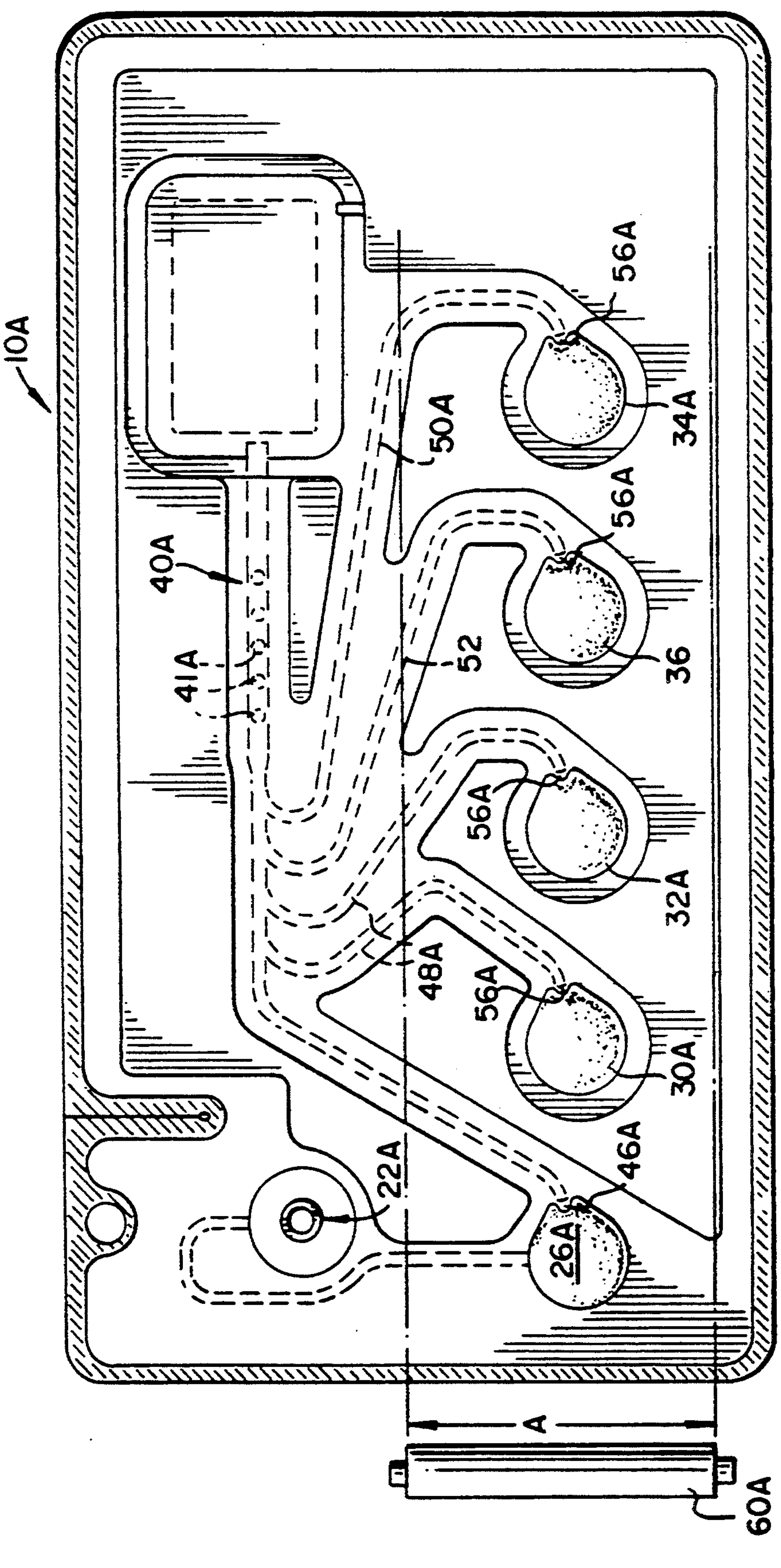
FIGS. 2 and 3 are plan views similar to that of FIG. 1, but showing alternate forms of the invention.

In either of the embodiments, the wash compartment can be supplemented, if desired, with additional wash liquid. A convenient method of doing this, FIG. 2, is to add a wash compartment adjacent to the first wash compartment, so that initially the first wash compartment is emptied to the detection site, and then the second wash compartment. Parts similar to those previously described bear the same reference numeral, to which the distinguishing suffix "A" is appended.

Thus, pouch 10A involves the exact same features as in the embodiment of FIG. 1, except that an additional temporarily-sealed compartment 36 of wash liquid is interposed between compartments 32A and 34A. Passageway 52 connects it to compartment 40A, after seal 56A of compartment 36 is burst.

Alternatively, a single wash compartment but with a greater volume of wash, can be used.

Figure 3:
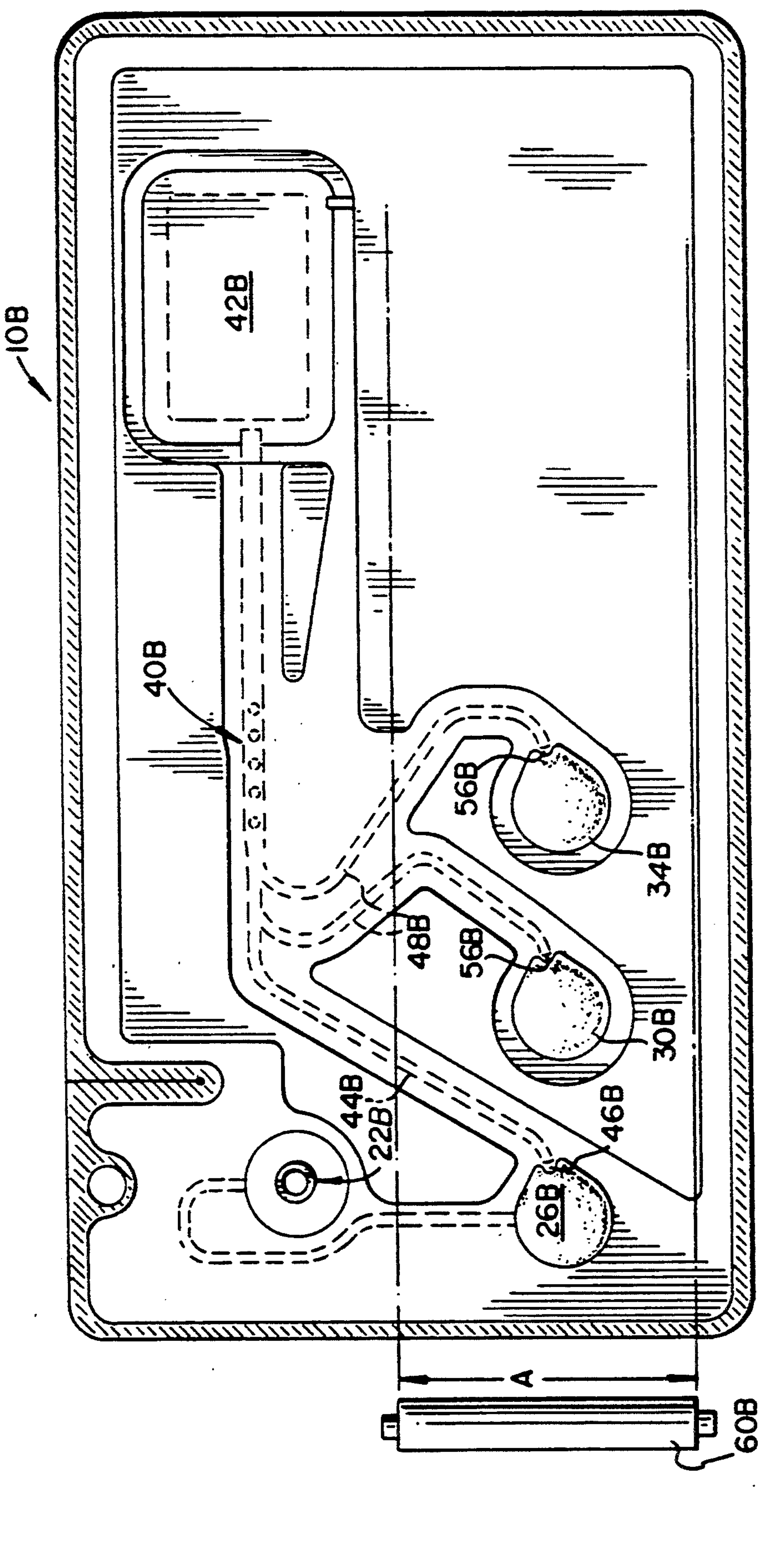

It is not necessary that there be any wash compartment or any wash step resulting, as shown in FIG. 3. Parts similar to those previously described bear the same reference numeral, to which the distinguishing suffix "B" is appended.

Thus, FIG. 3, pouch 10B comprises all the features of the previously described embodiments, except there is no wash compartment at all. The only compartments are the thermal cycling reaction compartment 26B, the label-containing compartment 30B (with, for example, streptavidin horseradish peroxidase, and compartment 34B containing the signalling material, e.g., $H_2O_2$, optionally a shear-thinning gel described immediately hereafter, and a leuco dye that reacts with the label enzyme to produce a dye. When seals 46B and 56B are burst sequentially by roller 60B, the contents empty via passageways 44B and 48B, respectively, into detection site 40B and then into waste compartment 42B.

In all of the embodiments, an optional ingredient for inclusion with the signalling material is an approximate 0.5% agarose solution, to stabilize color formation at the detection sites in the detection compartment. Agarose has the shear thinning behavior that its viscosity at about this concentration drops about 27 poise between a shear rate of 1 to $10^2$ $sec^{-1}$ (more than 60% of its drop), and only another 3 poise for rates above $10^2$, when measured at about 40° C. Other shear-thinning gels of similar viscosity behavior and low percentage concentration can also be used.

Figure 4A:
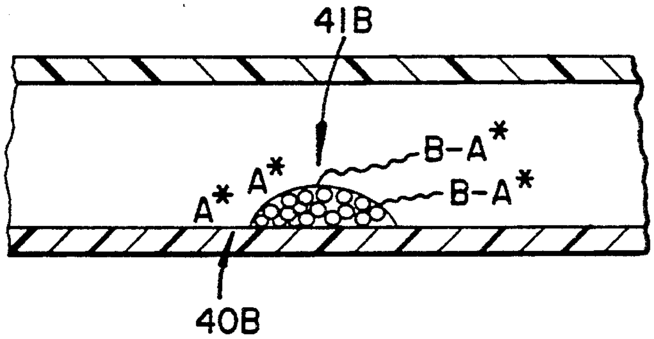
FIGS. 4A–4C are fragmentary section views illustrating a postulated mechanism for the invention.
Figure 4B:
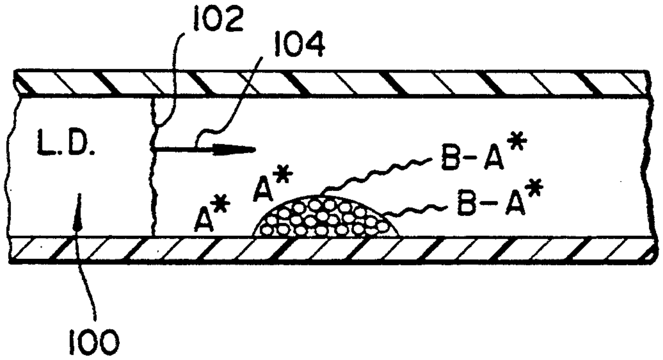
Figure 4C:
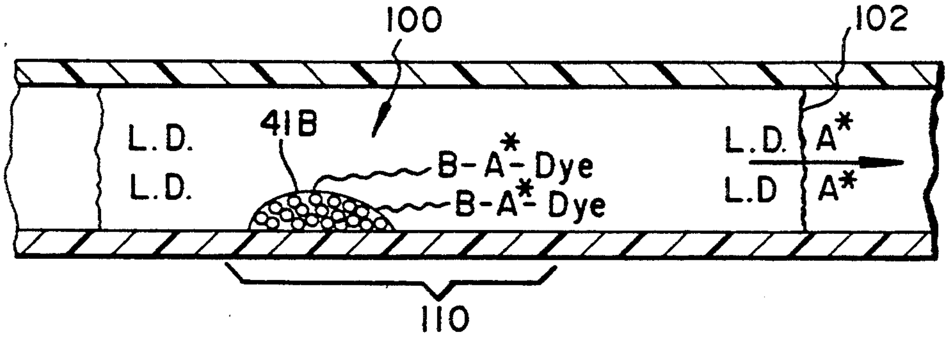

As noted above, it is not completely understood how the pouch surprisingly allows the wash steps to be eliminated, when heretofore they were considered essential between the addition of either the amplified material or the label, and the next reagent, to the detection site. FIGS. 4A-4C are included to help illustrate a postulated mechanism, using, e.g., the embodiment of FIG. 3. However, the same principal is believed to be operative in all embodiments.

What is shown is an enlarged detection site 41B, comprising immobilized beads as described in the aforesaid EPA 381,051. At the stage shown in FIG. 4A, the amplified target nucleic acid material with a biotin tail is shown as "~~~B". Such material has already been hybridized to the beads. Additionally, the compartment containing the label SA-HRP has been emptied to that site. (SA-HRP is shown as "A*" as a labeled avidin.) Some of that SA-HRP has already bound to the biotin of the target, but some is shown as unbound or "loose" on the beads and on the surface of compartment 40B.

When the next compartment, containing signalling material such as leuco dye (shown as "L.D.") is burst, the leuco dye advances as a "slug" 100, FIG. 4B. Its leading meniscus 102 approaches site 41B because of its motion, arrow 104. When "slug" 100 passes over site 41B, FIG. 4C, it sweeps off the unbound previous reagent (the A*) at meniscus 102, leaving only the bound label to react at the trailing part of slug 100 to produce dye at site 41B. Because it is region 110 that is read or detected, any extraneous dye produced downstream (at meniscus 102) is irrelevant. Backwards migration of such extraneous dye to the detection site is further retarded by the use of the optional shear-thinning gel described above.

EXAMPLES

The following non-exhaustive examples will help illustrate the invention.

All examples and comparative examples had reagents prepared as follows, unless otherwise noted:

A. Preparation of an HUT/HIV Analyte for Evaluation

HUT/AAV/78 cells containing one copy of HIV per cell were treated in a standard phenol chloroform extraction process to isolate the DNA, and the amount of DNA obtained was quantified on a spectrophotometer. The recovered DNA (100,000 copies HIV) was amplified by polymerase chain reaction (PCR) in a cocktail containing each of the primers identified below (1 $\mu$M each), buffer [10 mM magnesium chloride, 50 mM tris(-hydroxymethyl)aminomethane (TRIS), 50 mM potassium chloride, and 0.1 mg/mL gelatin], 1.5 mM of each of dATP, dCTP, dGTP, and dTTP deoxynucleotide triphosphates, and 40 units of DNA polymerase obtained from *Thermus aquaticus*.

Two sets of primers were used, one set complementary to the ENV region, and one set complementary to the GAG region of the HUT/HIV DNA, as is known to be used in multiplexing. One primer in each set was biotinylated to facilitate detection. Two tetraethylene glycol spacer groups were attached to the oligonucleotide according to the teaching of US-A-4,914,210.

Figure 7:
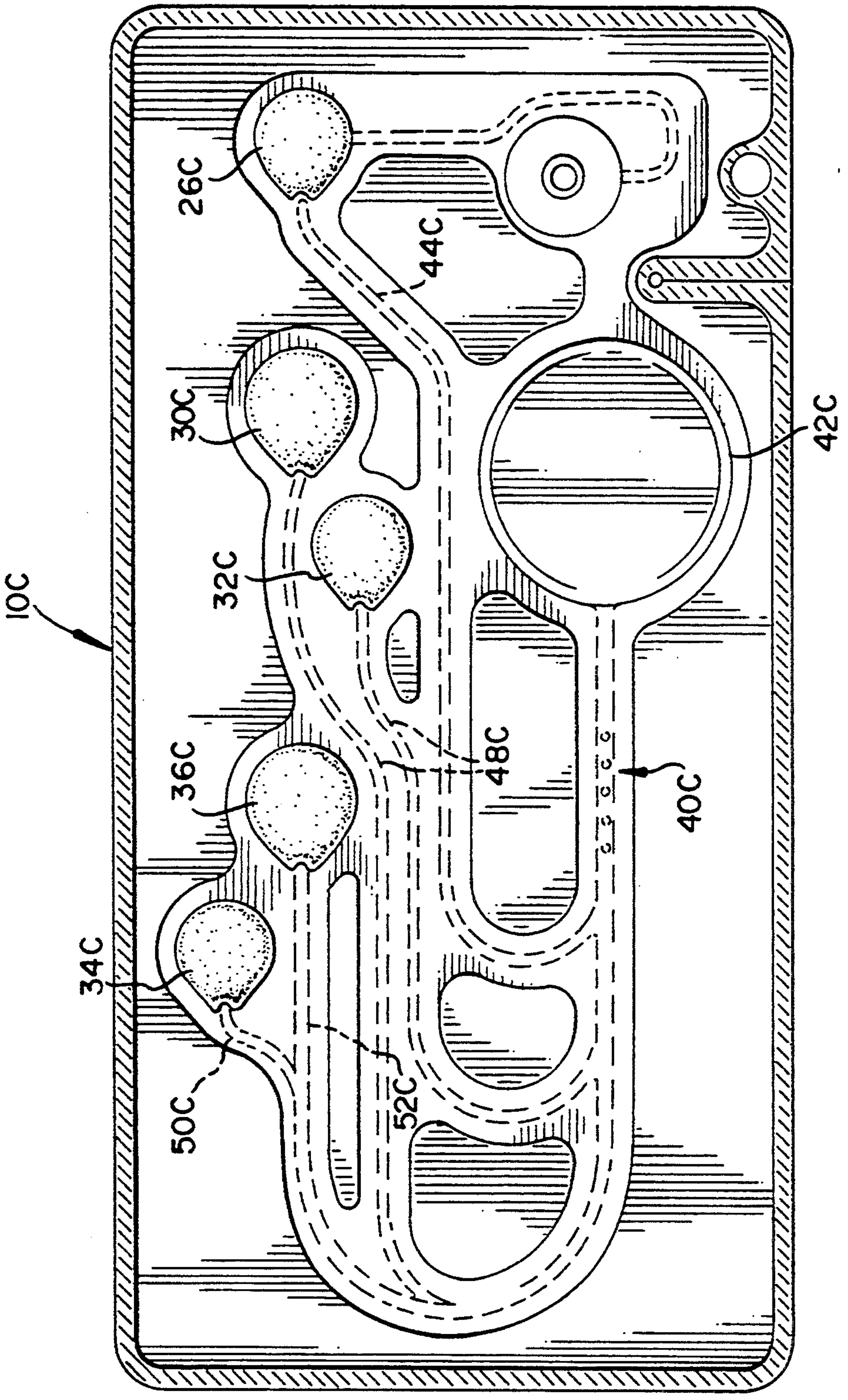
FIG. 7 is a plan view similar to that of FIG. 2, but showing a modified pouch used for the working examples.

The PCR protocol was carried out using 250 $\mu$L of the above cocktail in the PCR reaction blisters of PCR analytical elements of the type described in P. N. Schnipelsky et al. EPA 381,051 and U.S. patent application Ser. No. 673,053 filed on Mar. 21, 1991 (now allowed). More specifically, the pouch 10C of FIG. 7 was used. Parts similar to those previously described bear the same reference numeral with the letter "C" appended. Thus, compartments 26C, 30C, 32C, 36C and 34C; passageways 44C, 48C, 50C and 52C; detection site 40C, and waste compartment 42C were used as described above, except for the layout, or as noted hereinafter. For one thing, PCR amplification was done in a pouch separate from the test pouch 10C, with the amplified material being pooled and then injected into compartment 26C for consistency of results in all replicates, e.g., 32 in Ex. 1.

A thermal cycling processor of the type described in European Patent Application 402,994 was used.

The target DNA was preheated to 90° C. for ten seconds, then denatured at 96° C. for 30 seconds and cooled to 70° for 60 seconds to anneal primers and produce primer extension products. The latter two steps (heating at 96° C., then 70° C.) were repeated for a total of 40 cycles. This PCR process was replicated 64 times, and the fluid containing the newly made PCR product was transferred from the 64 PCR blisters into a common vessel to create a pool of PCR product. Samples from this pool were diluted 1:20 in the PCR buffer described above for use in the tests described hereinafter.

B. Preparation of Wash Solution (Where Used)

A wash solution was prepared to contain 1% sodium decyl sulfate in phosphate buffered saline solution containing 10 mmolar sodium phosphate, 150 mmolar sodium chloride, and 1 mmolar ethylenediaminetetraacetic acid, pH 7.4.

C. Preparation of Streptavidin/Horseradish Peroxidase (SA-HRP) Conjugate Solution A conjugate of streptavidin and horseradish peroxidase obtained from Zymed Labs (San Francisco, Calif.) was diluted 1:8000 with casein (0.5%) in a phosphate buffer solution (pH 7.3) containing thimerosal preservative (0.01%).

Preparation of Leuco Dye Composition

A solution of 25 g of polyvinylpyrrolidone in 100 mL of water was mixed with a solution of 0.20 g of 4,5-bis (4-dimethylaminophenyl)-2-(4-hydroxy-3,5-dimethoxyphenyl)imidazole blue-forming leuco dye in 1 mL N,N-dimethylformamide and stirred for 1 hour. This was then added to a solution prepared by mixing 2.76 g of monosodiumphosphate, monohydrate dissolved in 1900 mL of water, 0.2 mL of diethylenetriaminepentaacetic acid solution (0.1 M), and 1.51 g of 4'-hydroxyacetanilide and adjusting to pH 6.82 with 50% sodium hydroxide solution. Then 2 mL of 30% hydrogen peroxide was added and the mixture stirred to form a dye dispersion. Finally, 24.75 mL of the resulting dye dispersion was mixed with 0.25 mL of aqueous 25 μM dimedone and 0.125 g of agarose to produce a dye-forming composition containing 0.5% agarose. The total composition was heated and stirred at 80° C. until the agarose dissolved, and then cooled to room temperature.

E. Preparation of Probe Reagents

A poly[styrene-co-3-(p-vinylbenzylthio)propionic acid] (mole ration 97.6:2.4, weight ratio 95:5, 1 μm average diameter) aqueous polymer particle dispersion was prepared, and an oligonucleotide described hereinafter was covalently bound to one portion of the polymer particles, and another oligonucleotide was covalently bound to another portion of the polymer particles using the procedures described in U.S. patent application Ser. No. 654,112 (filed Feb. 12, 1991 by Ponticello et al) and in EPA 462,644 by Sutton et al. The oligonucleotides were linked to the polymer particles through two tetraethylene glycol spacers, a 3-amino-1,2-propanediol moiety, and a thymine base. Each oligonucleotide was appended to the polymer particles through the amino group of the 3-amino-1,2-propanediol moiety to form reagents by the procedures of U.S. Pat. No. 4,962,029.

The polymer/oligonucleotide particle probes were mixed with a latex adhesive of poly(methyl acrylate-cosodium 2-acrylamido-2-methylpropanesulfonate-co-2-acetoacetoxyethyl methacrylate) (90:4:6 weight ratio) at a dry weight ratio of particles to adhesive polymer of about 4/0.1 (2.5% adhesive). The aqueous dispersion had a solids content of about 4%.

These reagent formulations were used to prepare a series of analytical devices containing the reagents as capture probes in assays for HUT/HIV. The control reagent oligonucleotide sequence is a sequence from the HIV genome and was employed as a nonsense sequence. This nonsense probe should not capture any of the HUT/HIV analyte sequences, and consequently, no dye development should occur on the control reagents. The other probe reagent sequence was complementary to a sequence in the ENV region of the HUT/HIV DNA.

The above reagents were used to prepare a series of analytical elements (pouches), each having reagent compartments (one of which is a PCR reaction blister into which the sample analyte is first introduced) a detection compartment, and a waste reservoir. The analytical devices (or elements) were prepared by heating a sheet of poly(ethylene terephthalate)/polyethylene laminate (SCOTCHPAK™ 241, 3M Co.) at a forming station (or mold) to form an array of depressed areas (blisters) toward one side of the sheet, and a larger depressed area near the end, and at the other side of the sheet, to which a main channel ultimately leads, a main channel from the first blister to the last, and tributary channels from each blister to the main channel so that upon lamination to a cover sheet at a later time, the resulting pouch had narrow channels leading from the depressed areas to a main channel analogous to the devices described in said U.S. patent application Ser. No. 673,053 by Schnipelsky et al. Each depressed area except the one at each end of the main channel was filled with an appropriate reagent composition. A cover sheet was laminated to form a cover over the depressed and channel areas, and sealed to create a burst seal between each depressed area (except the last one) and the channel leading from it to the main channel. First, however, the cover sheet was treated overall with corona discharge. The probe reagent formulations described above (Invention & Control) were then immediately deposited in four alternating spots on the treated surface, each spot having 0.9 to 1.1 μL of formulation noted hereinafter, in a row. The disposed formulations were dried for about 30 seconds in a stream of air at room temperature while heating the opposite side of the support with an iron at about 95° C.

EXAMPLE 1

Wash Compartments Only Between Label Compartment and Signalling Material Compartment To demonstrate the embodiment of FIG. 2, 16 replicates were prepared. The blisters of each one of the sheets in the 16 replicates prepared above were filled with reagents in the example tests as follows:

| Blister (FIG. 7) | Reagent |
|---|---|
| 26C | Reserved for injection of analyte (~190-210 μL) |
| 30C | SA-HRP conjugate (~350 μL) |
| 32C | Wash solution (~235 μL) |
| 36C | Wash solution (~350 μL) |

-continued

| Blister (FIG. 7) | Reagent |
|---|---|
| 34C | Leuco dye (~235 μL) |

(Thus, extra wash material was supplied, but effective only to separate blister 5 from blister 2, and not effective to separate blister 2 from blister 1.)

As a comparative example akin to those shown in EPA 381,501 (the "stop solution" compartment having been omitted, a step clearly unnecessary for prompt readings), another set of 16 replicate pouches were prepared identical to Example 1, except that the positions of the first wash and the SA-HRP conjugate in blisters 2 and 3 and the amounts of each were reversed, i.e., 350 μL of wash solution and 235 μL of SA-HRP solution were used.

The cover sheet was then laminated and sealed in three steps. First, the sandwich was pressed and sealed by heating at about 149° C. only around the blisters containing the reagent solutions and around the waste blister. The formation of the sample-receiving PCR blister, including burst seals, and the channels was completed by heating the test pack between appropriately shaped heating jaws at about 163° C. The third step was the formation of perimeter seals around the test pack, and resealing all blister perimeter seals using a top plate temperature of 199° C. while the bottom plate remained at ambient temperature. The channels and blisters formed in the completed test pack (or element) were located so that passage of a roller across the portion of the element containing the reagent blisters would sequentially burst the seals of the blisters and force the reagent from each blister into and along an exit channel to the main channel leading to the area containing the capture probes. The finished element was inverted so that the cover sheet containing the capture probe spots (deposits) is the bottom of the finished element with the probe deposits properly aligned in the main channel to form a detection station. The four probe spots were located in different positions of the main channel in several samples.

A last waste compartment located at the end of the main channel was larger than the others and fitted with an absorbent to be a reservoir for waste fluids, for both Example 1 and the Comparative Example.

The completed pouches of Example 1 and the Comparative Example were used to evaluate the reagent formulations as follows:

A blister in each test device was filled (190–210 μL) with a 20X dilution of the PCR product described above and processed as follows:

EXAMPLE 1

The analyte was preheated to 95° C. for 120 sec. and its blister rolled to break the seal and advance the solution to the detection station (probe deposits). The analyte and probe reagents were hybridized in the detection station at 42° C. for 5 minutes, while the SA-HRP conjugate in the second blister was preheated to 65° C. The conjugate blister was rolled, the seal broken, and the solution directed to the detection area to displace the analyte. After 5 minutes, the third blister containing the first wash solution preheated to 55° C. was broken and the wash directed to the detection station and held there for 5 minutes while the second wash solution was preheated to 55° C. Then the blister containing the second wash solution was broken and the wash directed to the detection station. Finally, the blister containing the dye signal-forming composition was rolled without preheating, and the seal broken, and the composition directed to the detection station where the color scores were read after a 5 minute incubation period using a color chart as described hereinbelow. The color scores are recorded in Table I and presented graphically in FIG. 5A.

THE COMPARATIVE EXAMPLE

The blister containing the analyte in each element was preheated to about 95° C. for 120 seconds and then rolled to break the seal and advance the solution to the area containing the four immobilized deposits of probe reagents, i.e., the two control probes and the two HUT/HIV probes deposited with adhesive. The analyte and probe reagents were hybridized in the detection station at 42° C. for 5 minutes, while the blister containing the wash solution was preheated to 55° C. Then the wash solution blister was rolled to break the seal and direct the wash solution into the detection area to clean out the main channel and to remove unbound analyte from the detection area. Then, without preheating, the seal of the streptavidin/horseradish peroxidase conjugate blister was rolled and broken and the solution directed to the detection area where it binds to the immobilized biotinylated analyte over a 5-minute period. During this time, the second wash composition was preheated to 55° C., and the seal of the blister was then broken with the roller and directed to the detection station where it displaced the unbound label. Finally, the seal of the dye signal-forming composition in the last blister was broken with the roller, and the fluid directed to the detection station where it displaced the second wash solution. Dye formation on the probe deposits was allowed to proceed for 5 minutes before reading color density scores. The color of each probe deposit was evaluated by comparison of the wet dye density with a color chart where 0 is no density and 10 is the highest density. The color scores are recorded in Table II and presented graphically in the graph of FIG. 5B. (The letters "LTR" and "ENV" of Tables I and II represent, respectively, the control nonsense probe deposits and the probe deposits complementary to the ENV region of the HIV genome in the analyte. These represent each of the 4 bead sites in the detection compartment. Left to right, the first bead encountered by flowing liquid was "LTR" The second was "ENV"; "third", and finally the last, "ENV" in the right hand column.)

TABLE I

| | Example 1 - HIV | | | |
|---|---|---|---|---|
| REPLICATE | LTR | ENV | LTR | ENV |
| 1 | 0.5 | 7 | 0.5 | 6.5 |
| 2 | 0 | 6.5 | 0 | 4 |
| 3 | 0.5 | 6.5 | 0.5 | 6.5 |
| 4 | 1 | 6.5 | 1 | 6.5 |
| 5 | 1 | 6.5 | 1 | 6.5 |
| 6 | 0.5 | 6.5 | 0.5 | 6 |
| 7 | 0.5 | 5 | 0.5 | 5.5 |
| 8 | 0.5 | 6.5 | 0.5 | 6 |
| 9 | 1 | 5 | 1 | 4 |
| 10 | 0.5 | 5 | 0.5 | 5 |
| 11 | 0.5 | 7 | 0.5 | 6.5 |
| 12 | 0.5 | 6 | 0.5 | 6 |
| 13 | 0.5 | 7 | 0.5 | 6.5 |
| 14 | 0.5 | 6 | 0.5 | 7 |
| 15 | 0.5 | 2 | 0 | 2 |
| 16 | 0.5 | 7 | 0.5 | 6.5 |

TABLE I-continued

| | Example 1 - HIV | | | |
|---|---|---|---|---|
| REPLICATE | LTR | ENV | LTR | ENV |
| Average | | 6.0 | | 5.69 |

TABLE II

| | Comparative Example - HIV | | | |
|---|---|---|---|---|
| REPLICATE | LTR | ENV | LTR | ENV |
| 1 | 0.5 | 5 | 0.5 | 5.5 |
| 2 | 0.5 | 2 | 0.5 | 6 |
| 3 | 0.5 | 6.5 | 0.5 | 5.5 |
| 4 | 1 | 6 | 1 | 6 |
| 5 | 0.5 | 2 | 0.5 | 2 |
| 6 | 1 | 7 | 1 | 6 |
| 7 | 1 | 7 | 1 | 5 |
| 8 | 1 | 7 | 1 | 6 |
| 9 | 1 | 3 | 1 | 7 |
| 10 | 1 | 7 | 1 | 6 |
| 11 | 0.5 | 1 | 0.5 | 4 |
| 12 | 1 | 7 | 0.5 | 6 |
| 13 | 1 | 7 | 1 | 6.5 |
| 14 | 0.5 | 6 | 1 | 4 |
| 15 | 1 | 6.5 | 1 | 6 |
| 16 | 1 | 7 | 1 | 5.5 |
| Average | | 5.44 | | 5.44 |

Figure 5A:
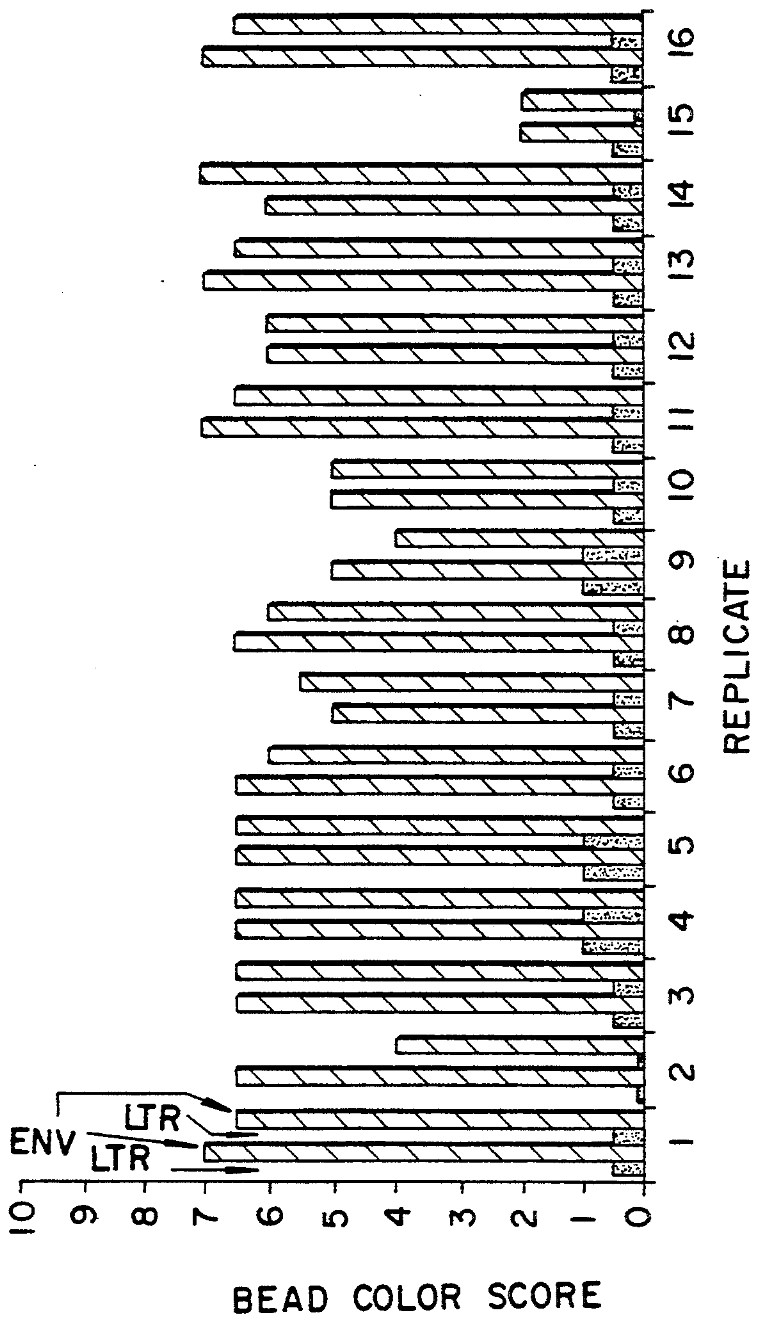
FIGS. 5A–5B and 6A–6B are graphs showing repetitive color scores achieved during the practice of the invention (5A, 6A and 6B) or of a comparative example (5B)
Figure 5B:
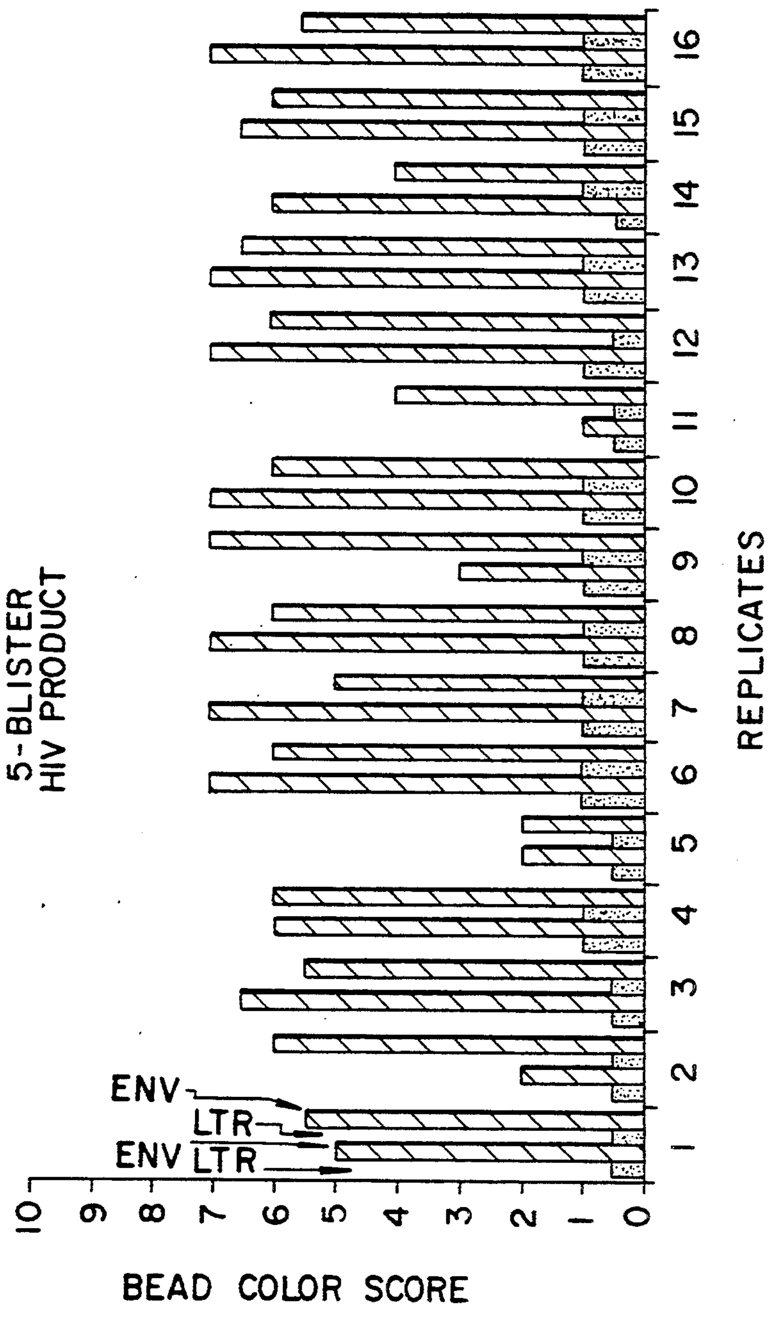

As is readily apparent, particularly from a comparison of FIGS. 5A and 5B, the elimination of the wash step after hybridizing the amplified nucleic acid material to the detection site and before adding the label reagent, did not harm the results. Indeed, better results occurred. Quantitatively, this can also be seen by averaging the second and fourth beads "ENV" in Example 1 for all 16 replicates, and comparing those with the Comparative Example. For Example 1, the average was 6.0 and 5.69, whereas for the Comparative Example it was 5.44 in both cases.

The above results are not limited to a particular assay—they also occur when assaying for, e.g., CMV (cytomegalovirus). It is for this reason that the oligonucleotide sequences have not been specifically identified as it is believed to be immaterial which assay is used to show that one or both washes can be eliminated.

It has been shown that results comparable to those of Example 1 occur if the second wash compartment is omitted, to produce a pouch as shown in FIG. 1. That is, in such a pouch a wash compartment and step occurs only between the label compartment and step (using SA-HRP) and the signalling material compartment and step (using a leuco dye and $H_2O_2$).

Similarly, it has been shown that such a 4-compartment pouch with only one wash compartment, but located between the reaction compartment used to amplify the nucleic acid material, and the label compartment, produces results that are comparable to the conventional construction having a wash compartment (and step) after each of the reaction compartment (hybridizing step) AND the label compartment (labeling step).

EXAMPLE 2

Comparison of the Pouches of Example 1 with Pouches Containing no Wash Solutions Two sets of PCR analytical pouches were prepared by the procedures of Example 1 with the following exceptions:

1. A third probe composition was prepared by the procedures of Example 1 to contain a sequence complementary to a sequence from the GAG region of the HUT/HIV DNA.
2. Only one spot (deposit) of each of the 3 probes was incorporated in each element, in the order of (1) new probe from the GAG region as described above, (2) control probe of Example 1, and (3) reagent probe of Example 1.
3. One set of pouches was 5-blister pouches in the reverse wash format of Example 1 (SA-HRP conjugate in the second blister and wash in the third blister), and the pouches in that set were processed as described in Example 1.
4. The second set of pouches used only 3 reagent compartments and no wash compartments, as shown in FIG. 3. They contained the same compositions, including the analyte composition from the pool, and same amounts as the corresponding compositions in the first set of elements of Example 1 (the set with the conventional wash format), and the blisters were in the following order:

| Blister (FIG. 7) | Content |
|---|---|
| 26C | PCR analyte |
| 30C | SA-HRP |
| 32C | Dye-forming detection composition |

The remaining blisters or compartments were left empty.

Figure 6B:
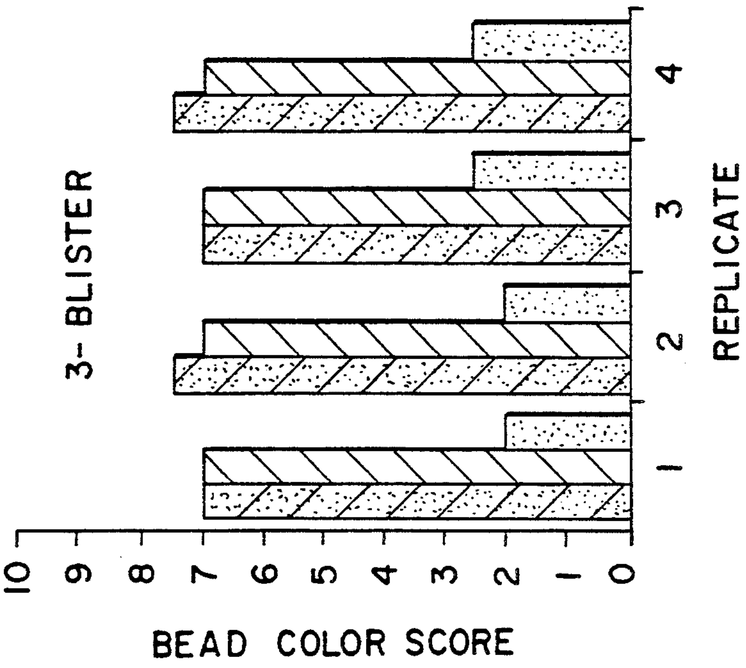
Figure 6A:
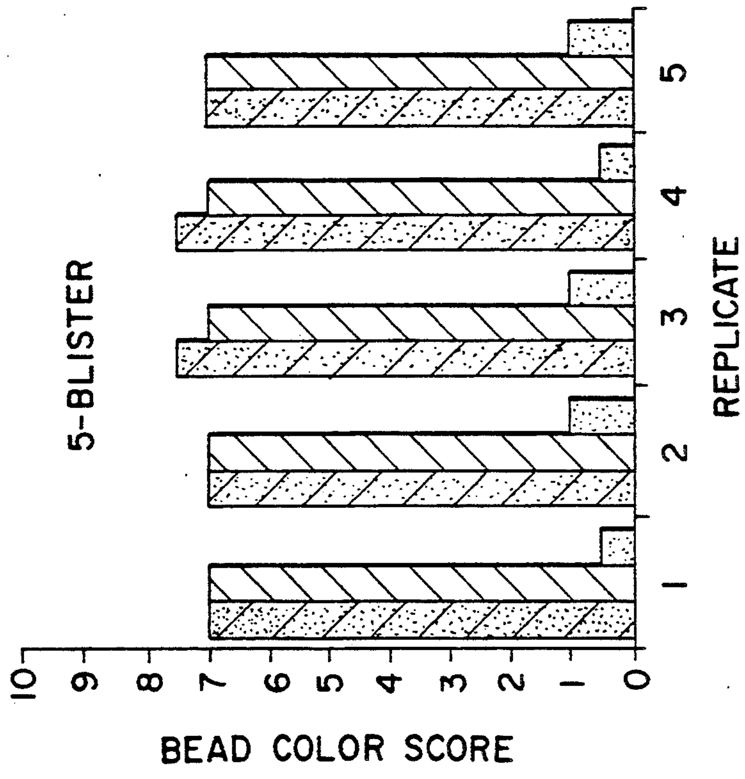

The pouches in the second set were processed as follows:

The analyte in the PCR blister was preheated to 95° C. for 120 seconds, and the blister was rolled to break the seal and direct the analyte to the 3 probe deposits in the detection station. Hybridization at 42° C. was allowed to proceed for 5 minutes while the SA-HRP solution in the second blister was preheated to 65° C. The second blister was then rolled to break the seal and the solution directed through the channels to the detection station. The conjugate was incubated over the detection station for 5 minutes, then the blister containing the dye-forming detection dispersion was rolled without preheating to break the seal and direct the dispersion to the detection station to displace the SA-HRP. After 5 minutes incubation of the dye dispersion in the detection station, the color scores were read using a color chart as in Example 1. The color scores for both sets of elements are recorded in Tables IIA and IIB and are presented graphically in the Graphs of FIGS. 6A and 6B, respectively.

The data show that the 3-blister pouch configuration gives positive signals comparable to those of the 5-blister, wash pouch format of Example 1; however, with slightly elevated signals on the nonsense (control) beads. This can be reduced or eliminated in the 3-blister configuration by using a larger volume of the dye-forming detection dispersion. The 3-blister configuration allows for use of less reagents, a smaller unit manufacturing cost, less pouch storage space, shorter processing times, and a smaller, less complex processor.

TABLE IIA

| 5-Blister as with Example 1 | | | |
|---|---|---|---|
| REPLICATE | GAG | ENV | LTR |
| 1 | 7 | 7 | 0.5 |
| 2 | 7 | 7 | 1 |

TABLE IIA-continued

| | 5-Blister as with Example 1 | | |
|---|---|---|---|
| REPLICATE | GAG | ENV | LTR |
| 3 | 7.5 | 7 | 1 |
| 4 | 7.5 | 7 | 0.5 |
| 5 | 7 | 7 | 1 |

TABLE IIB

| | 3-Blister Data | | |
|---|---|---|---|
| REPLICATE | GAG | ENV | LTR |
| 1 | 7 | 7 | 2 |
| 2 | 7.5 | 7 | 2 |
| 3 | 7 | 7 | 2.5 |
| 4 | 7.5 | 7 | 2.5 |

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. In a device for amplidying and detecting nucleic acid material in a closed container by using at least one target strand as a template, said device comprising a reaction compartment containing reagents for amplifying a sample of nucleic acid material, a detection site for detecting amplified nucleic acid material, and storage compartments containing a label and signaling material effective to generate, in combination, a detectable signal, and passageways for fluidly connecting said compartments with said site but closed to the environment, the improvement wherein said device is free of any wash compartment containing a wash liquid substantially free of capture, label, and signal-forming reagents used in storage or reaction compartments, so that no wash stem is used in a sequence of steps comprising the emptying and moving of the contents of said compartments to said detection site.

2. A device as defined in claim 1, wherein all of said compartments, detection site, and passageways are sealed against leakage to the exterior of said device to prevent carry-over contamination.

3. A device as defined in claims 1or wherein said label is an enzyme.

* * * * *

UNITED STATES PATENT AND TRADEMARK OFFICE

CERTIFICATE OF CORRECTION

PATENT NO. : 5,422,271

DATED : June 6, 1995

INVENTOR(S) : Lynn Bergmeyer

It is certified that error appears in the above-indentified patent and that said Letters Patent is hereby corrected as shown below:

Column 14, line 2, after "for", delete "amplidying" and insert --amplifying--.

Column 14, line 17, after "wash", delete "stem" and insert --step--.

Column 14, line 23, after "claims", delete "1or" and insert --1 or 2,--.

Signed and Sealed this

Tenth Day of October, 1995

Attest:

Bruce Lehman

BRUCE LEHMAN

*Attesting Officer* *Commissioner of Patents and Trademarks*